United States Patent
Whitehurst et al.

(10) Patent No.: US 7,877,137 B2
(45) Date of Patent: *Jan. 25, 2011

(54) THROMBOLYSIS AND CHRONIC ANTICOAGULATION THERAPY

(75) Inventors: Todd K Whitehurst, Santa Clarita, CA (US); Kelly H McClure, Simi Valley, CA (US); James R Thacker, Eureka, MO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 319 days.

This patent is subject to a terminal disclaimer.

(21) Appl. No.: 11/949,752

(22) Filed: Dec. 3, 2007

(65) Prior Publication Data

US 2008/0286327 A1 Nov. 20, 2008

Related U.S. Application Data

(63) Continuation of application No. 10/285,803, filed on Nov. 1, 2002, now Pat. No. 7,308,303.

(60) Provisional application No. 60/340,076, filed on Nov. 1, 2001.

(51) Int. Cl.
A61N 1/08 (2006.01)

(52) U.S. Cl. .................................................. 607/3

(58) Field of Classification Search ............ None
See application file for complete search history.

(56) References Cited

U.S. PATENT DOCUMENTS

| 4,232,679 A | 11/1980 | Schulman |
| 4,408,608 A | 10/1983 | Daly et al. |
| 4,481,950 A | 11/1984 | Duggan |
| 4,608,985 A | 9/1986 | Crish et al. |
| 4,628,942 A | 12/1986 | Sweeney et al. |
| 4,649,936 A | 3/1987 | Ungar et al. |
| 4,793,353 A | 12/1988 | Borkan |
| 5,193,539 A | 3/1993 | Schulman et al. |
| 5,193,540 A | 3/1993 | Schulman et al. |
| 5,199,428 A | 4/1993 | Obel et al. |
| 5,305,745 A * | 4/1994 | Zacouto ...................... 600/324 |
| 5,314,458 A | 5/1994 | Najafi et al. |
| 5,324,316 A | 6/1994 | Schulman et al. |

(Continued)

FOREIGN PATENT DOCUMENTS

WO    WO98/37926    9/1998

(Continued)

*Primary Examiner*—Carl H. Layno
*Assistant Examiner*—Jon-Eric C. Morales
(74) *Attorney, Agent, or Firm*—Frommer Lawrence & Haug LLP; Bruce E. Black

(57) ABSTRACT

Method and systems of treating a patient with at least one of a myocardial infarction, a stroke, and a pulmonary embolism include providing a stimulator coupled to at least one electrode and a catheter, configuring one or more stimulation parameters to treat at least one of a myocardial infarction, a stroke, and a pulmonary embolism, programming the stimulator with the one or more stimulation parameters, delivering with the stimulator via the catheter at least one drug to at least one tissue in accordance with the one or more stimulation parameters, and limiting perfusion of the at least one tissue by delivering electrical stimulation with the stimulator via the at least one electrode to the at least one tissue.

20 Claims, 5 Drawing Sheets

U.S. PATENT DOCUMENTS

| | | | |
|---|---|---|---|
| 5,338,662 A | 8/1994 | Sadri | |
| 5,358,514 A | 10/1994 | Schulman et al. | |
| 5,405,367 A | 4/1995 | Schulman et al. | |
| 5,494,822 A | 2/1996 | Sadri | |
| 5,716,318 A * | 2/1998 | Manning | 600/16 |
| 5,725,563 A | 3/1998 | Klotz | |
| 5,755,750 A | 5/1998 | Petruska et al. | |
| 5,895,416 A | 4/1999 | Barreras et al. | |
| 5,916,154 A | 6/1999 | Hobbs et al. | |
| 6,051,017 A | 4/2000 | Loeb et al. | |
| 6,058,331 A | 5/2000 | King | |
| 6,073,048 A | 6/2000 | Kieval et al. | |
| 6,154,678 A | 11/2000 | Reno | |
| 6,178,349 B1 | 1/2001 | Kieval | |
| 6,205,359 B1 | 3/2001 | Boveja | |
| 6,216,045 B1 | 4/2001 | Black et al. | |
| 6,266,564 B1 | 7/2001 | Hill et al. | |
| 6,341,236 B1 | 1/2002 | Osorio et al. | |
| 6,356,777 B1 | 3/2002 | Garfield et al. | |
| 6,447,443 B1 | 9/2002 | Keogh et al. | |
| 6,464,687 B1 | 10/2002 | Ishikawa et al. | |
| 6,526,318 B1 | 2/2003 | Ansarinia | |
| 6,571,127 B1 | 5/2003 | Ben-Haim et al. | |
| 6,650,943 B1 | 11/2003 | Whitehurst et al. | |
| 6,712,753 B2 | 3/2004 | Manne | |
| 6,845,267 B2 | 1/2005 | Harrison et al. | |
| 6,907,295 B2 | 6/2005 | Gross et al. | |
| 6,928,320 B2 | 8/2005 | King | |
| 6,970,741 B1 | 11/2005 | Whitehurst et al. | |
| 7,308,303 B2 * | 12/2007 | Whitehurst et al. | 607/3 |
| 2001/0003799 A1 | 6/2001 | Boveja | |
| 2002/0016615 A1 * | 2/2002 | Dev et al. | 607/2 |
| 2002/0022873 A1 | 2/2002 | Erickson et al. | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0172089 A1 | 9/2004 | Whitehurst et al. | |
| 2005/0101878 A1 | 5/2005 | Daly et al. | |
| 2006/0292211 A1 * | 12/2006 | Hood et al. | 424/450 |

FOREIGN PATENT DOCUMENTS

| | | |
|---|---|---|
| WO | WO98/43700 | 10/1998 |
| WO | WO98/43701 | 10/1998 |

* cited by examiner

THROMBOLYSIS AND CHRONIC ANTICOAGULATION THERAPY

RELATED APPLICATIONS

The present application is a continuation application of U.S. application Ser. No. 10/285,803, filed Nov. 1, 2002, which issued as U.S. Pat. No. 7,308,303 on Dec. 11, 2007, which application claims the benefit of Provisional Application Ser. No. 60/340,076, filed Nov. 1, 2001. Both applications are incorporated herein by reference in their respective entireties.

BACKGROUND

Thrombolytic Therapy

Thrombolytic therapy is used to dissolve blood clots (i.e., thrombi). Thrombolytic agents include protein catalysts that activate a plasma proenzyme known as plasminogen to, in turn, produce the active enzyme plasmin. Plasmin then solubilizes fibrin and degrades a number of other plasma proteins, most notably fibrinogen and the procoagulant factors V and VII. Available thrombolytic agents include urokinase, tissue plasminogen activator (tPA), duteplase (a type of tPA), alteplase (a.k.a. activase, a type of tPA), streptokinase, anistreplase (also known as anisoylated plasminogen-streptokinase activator complex, or APSAC), and tenecteplase (a.k.a. TNKase, a type of tPA).

Indications for thrombolytic therapy include acute myocardial infarction, acute ischemic stroke, acute pulmonary embolism, acute deep venous thrombosis, and a clotted arteriovenous (AV) fistula or shunt. Bleeding is the major complication of thrombolytic therapy. Consequently, absolute contraindications include dissecting aortic aneurysm, pericarditis, hemorrhagic stroke, or neurosurgical procedures within six months or known intracranial neoplasm. Relative contraindications include major surgery or bleeding within six weeks, known bleeding diathesis, and severe uncontrolled hypertension. Streptokinase and anistreplase are potentially allergenic, so patients are usually prophylactically pre-treated with intravenous hydrocortisone.

Studies show that thrombolytic therapy administered within 24 hours of an acute myocardial infarction leads to decreased mortality and morbidity. Of the 900,000 people who have heart attacks in the United States every year, only one-fifth receive thrombolytic drugs of any kind and only one-tenth receive tPA. Streptokinase, an effective clot buster sold at one tenth the price of tPA, is a popular rival of tPA.

A 1995 study showed that, for every 100 carefully selected patients with ischemic stroke and no CT evidence of intracranial hemorrhage treated with tPA within three hours after stroke onset, an additional 12 recover without residual disability. Some evidence suggests that the earlier this therapy is delivered, the more likely the patient is to recover neurological function.

Anticoagulation Therapy

Chronic anticoagulation therapy is used to prevent blood clots, e.g., in patients with a history of thromboembolism formation. The disorders treated with chronic anticoagulation therapy include acute venous thrombosis (e.g., deep venous thrombosis or DVT) or pulmonary embolism. (DVT usually refers to a blood clot in a deep vein of a limb, most commonly one of the legs.) Chronic anticoagulation therapy may also be used to prevent arterial thromboembolism associated with atrial fibrillation, left ventricular thrombus, and other disorders that have demonstrated a significant risk of thromboembolism (e.g., presence of lupus anticoagulant antibody and/or anti-cardiolipin antibody, and paradoxical embolism).

Chronic anticoagulation therapy is also used for prophylaxis of thromboembolism in asymptomatic patients with no history of thrombosis but with a disorder(s) or other risk factor(s) for forming a thromboembolism. Such disorders include chronic or paroxysmal atrial fibrillation, presence of a mechanical cardiac valve, post-operative venous thrombosis, post-myocardial infarction, cardiomyopathy, documented procoagulant disorder with first degree relative with DVT, and presence of a central venous catheter. Chronic anticoagulation therapy may also be used for prophylaxis of thromboembolism during chemotherapy in women with breast cancer.

Cardiovascular Disease

According to 1997 estimates, 60 million Americans have one or more forms of cardiovascular disease. Coronary heart disease affects approximately 12.2 million Americans, with 6.3 million afflicted with angina pectoris. An estimated 7.7 million Americans have suffered a myocardial infarction, and an additional 4.4 million have suffered a stroke. Many of these patients are on chronic anticoagulation therapy. A few were fortunate enough to receive thrombolytic therapy within a few hours following a myocardial infarction or a stroke.

Atrial Fibrillation

Atrial fibrillation (AF), the most commonly encountered arrhythmia in clinical practice, causes significant morbidity and mortality in affected individuals and is a considerable burden on healthcare services. Clinical manifestations range from palpitations through heart failure to cerebral embolism and ischemic stroke. AF is present in 17 to 25% of acute stroke patients and is estimated to increase stroke risk five-fold compared with patients in sinus rhythm.

Studies show that aspirin therapy has a modest benefit, reducing stroke rate by one-fifth, whereas warfarin limits annual incidence of stroke to 1.4%. Such anticoagulant therapy, however, can cause major hemorrhage at a rate of 2.3% per year.

The true prevalence of AF is difficult to establish, but is probably between 0.4 and 1.7% of the adult population, with approximately 20 to 30% of cases displaying a paroxysmal pattern. Community-based studies have demonstrated a male predominance and a striking relationship with increasing age—the prevalence rising from less than 1% at younger than 65 years, 2.3% at 65 to 69 years, 4.1% at 70 to 74 years, 5.8% at 75 to 79 years, 6.4% at 80 to 84 years, and 8.1% at older than 85 years of age. It has been estimated that there are 2.2 million cases of AF in the United States, with a median age of 75 years. Thus, AF is a common condition in the elderly and will only increase as the mean population age rises.

Deep Vein Thrombosis (DVT) and Pulmonary Embolism

Deep venous thrombosis (DVT) is a relatively common disease that is often encountered by family physicians. Epidemiologic data suggest that the annual incidence of a first episode of DVT ranges from 60 to 180 cases per 100,000 people, or more than 300,000 new cases annually in the United States. The cost burden of this disease is quite high, since most patients with DVT require one or more diagnostic tests, treatment with intravenous heparin, and a three- to seven-day hospital stay.

DVT is development of a thrombus of fibrin, red blood cells, platelets, and granulocytes within a deep vein. Thrombi form where blood flow is stagnant and where eddies form along the cusps of valves. The danger lies in pulmonary embolization through thrombus detachment. The embolus floats through veins of increasing diameter to the right side of the heart, where it is pumped to the pulmonary arterial system in the lungs; the embolus lodges where its diameter is greater than the lumen of the artery.

An estimated 500,000 people in the United States will suffer from some degree of pulmonary emboli (PE) this year, and 50,000 will die as a result. Not all PEs are life-threatening; in fact, many people unknowingly have had one or more PEs. The outcome of any PE depends largely on the length, diameter, and number of emboli carried to the lungs. Large emboli are usually 1.0 to 1.5 cm in diameter and can commonly be 5 cm long. The origin of most major PE is the ilio-femoral veins, with relatively fewer coming from the calf veins and the inferior vena cava.

Paradoxical Embolism

Paradoxical embolism is the passage of a clot (thrombus) from a vein to an artery. As described above, when clots in veins break off (embolize), they travel to the right side of the heart and then, normally, to the lungs, where they lodge. The lungs prevent clots from entering the arterial circulation. However, when there is a hole in the wall between the two upper chambers of the heart (an atrial septal defect), a clot can cross from the right to the left side of the heart, then into the arteries as a paradoxical embolism. Once in the arterial circulation, a clot can travel to the brain, block a vessel there, and cause a stroke (cerebrovascular accident). Because of this risk of stroke from paradoxical embolism, even small atrial septal defects are usually repaired.

Warfarin (Coumadin®)

Warfarin is the most frequently prescribed oral anticoagulant, the fourth most prescribed cardiovascular agent, and the overall eleventh most prescribed drug in the United States, with annual sales of approximately $500 million. Nonetheless, in 1995, the Agency for Healthcare Policy and Research (AHCPR) reported that warfarin is greatly underutilized for stroke prevention.

Warfarin is an antagonist of vitamin K, a necessary element in the synthesis of clotting factors II, VII, IX and X, as well as the naturally occurring endogenous anticoagulant proteins C and S. These factors and proteins are biologically inactive without the carboxylation of certain glutamic acid residues. This carboxylation process requires oxidized vitamin K as a cofactor and occurs primarily in the liver. Antagonism of vitamin K or a deficiency of this vitamin reduces the rate at which these factors and proteins are produced, thereby creating a state of anticoagulation.

Therapeutic doses of warfarin reduce the production of functional vitamin K-dependent clotting factors by approximately 30 to 50 percent. A concomitant reduction in the carboxylation of secreted clotting factors yields a 10 to 40 percent decrease in the biologic activity of the clotting factors. As a result, the coagulation system becomes functionally deficient.

Warfarin prolongs the prothrombin time (PT), which is responsive to depression of three of the four vitamin K-dependent coagulation factors (factors II, VII, and X). The International Normalized Ratio (INR) has been developed and adopted as a method to standardize monitoring of oral anticoagulant therapy. The INR is less reliable as a measure of anticoagulation in the early course of warfarin therapy; however, it is more reliable than the PT or PT ratio for clinical management.

Warfarin does not affect established thrombus and does not reverse ischemic tissue damage. Warfarin therapy prevents further extension of the clot and prevents secondary thromboembolic complications.

Heparin

Heparin is a parenteral anticoagulant widely used in clinical medicine. Compared with low molecular weight heparins, unfractionated heparin produces a less predictable anticoagulant response due primarily to its reduced bioavailability after subcutaneous administration of low doses, its dose-dependent clearance, and differences among patients in the nonspecific binding of heparin to proteins and cells.

Heparin exerts its anticoagulant action by accelerating the activity of antithrombin III (ATIII). The interaction of heparin with ATIII produces a conformational change in ATIII, which accelerates the ability of ATIII to inactivate the coagulation enzymes thrombin (factor IIa), factor Xa, and factor IXa.

The activated partial thromboplastin time (APTT) is usually used to monitor heparin therapy since it is sensitive to the inhibitory effects of heparin on thrombin, factor Xa, and factor IXa. High doses of heparin interfere with platelet aggregation, which, in turn, prolongs bleeding time, although typical doses of heparin do not affect bleeding time.

Heparin does not lyse existing clots. It is important to achieve therapeutic heparin concentrations quickly following a pathological thrombus in order to prevent clot extension.

Prothrombin Time (PT) and International Normalized Ratio (INR) Measurement

The prothrombin time (PT) test essentially monitors the time it takes for a sample of blood to clot after the blood is exposed to a coagulation-promoting agent (thromboplastin). The result of a test is expressed as an International Normalized Ratio (INR), which was developed to reduce variability in PT test results. In order to make PT times comparable across labs, the World Health Organization (WHO) has designated an international reference preparation (IRP) of thromboplastin (rTF/95) as a standard. This allows commercial thromboplastins to be compared to a WHO reference standard and be corrected to adjust to the WHO reference by the International Sensitivity Index (ISI). The INR is then calculated according to the following formula: INR=(Patient PT in seconds/Mean Normal PT in seconds)^ISI.

An INR of 1 typically corresponds to normal blood coagulation. Assuming an ISI of 1, an INR of 2 means that the coagulation time is about twice as long as normal, an INR of 3 equates to about three times as long as normal, and so on.

Alternative Coagulation Assays to PT

In 1994, Le, et al. investigated other coagulation assays in 79 patients attending an anticoagulation clinic. [Le, et al. "The International Normalized Ratio (INR) for Monitoring Warfarin Therapy: Reliability and Relation to Other Monitoring Methods" *Annals of Internal Medicine,* 1 Apr. 1994; 120: 552-558.] Because determinations of residual specific prothrombin activity and native prothrombin antigen have been proposed as being better techniques for monitoring oral anticoagulant therapy than the prothrombin time, the authors examined the relation between these measurements and INR values. Specifically, they evaluated the Specific Prothrombin Assay and a Native Prothrombin Antigen Assay.

Specific Prothrombin Assay (Factor II): Prothrombin activity was assayed by a one-stage assay in which a mixture of 100 µL of a prothrombin-depleted human serum/barium-adsorbed bovine plasma reagent and 100 µL of a 1:10 to 1:40 dilution of test plasma were clotted by the addition of 200 µL of a thromboplastin C reagent containing $CaCl_2$. Clotting times were converted to percent normal plasma prothrombin activity from a log-log standard curve prepared with dilutions of control pooled plasma.

Native Prothrombin Antigen Assay: The authors measured plasma native prothrombin antigen concentration with native prothrombin antigen enzyme immunoassay kits. Color was measured at 450 nm with a Thermomax enzyme-linked immunosorbent assay reader.

Relations among Values for International Normalized Ratios, Native Prothrombin Antigen, and Specific Prothrombin Activity: The authors confirmed an earlier report of good correlation between residual plasma native prothrombin antigen levels measured by enzyme immunoassay and residual specific prothrombin activity measured by a one-stage coagulation method (r=0.92, n=89). A mean INR range of 2.0 to 3.0 corresponded to between about 40% to 20% residual native plasma prothrombin.

Activated Partial Thromboplastin Time (PTT) Measurement

The intrinsic capability of blood to form a fibrin clot requires coagulation factors XII (Hageman), XI (plasma thromboplastin antecedent), IX (Christmas), VII (anti-hemophilic), X (Stuart-Prower), V (proaccelerin), II (prothrombin), I (fibrinogen), platelet lipid, and calcium. Historically, intrinsic coagulation was measured by timing fibrin clot formation upon recalcification of citrated, anticoagulated, platelet rich plasma. Measurement with platelet rich plasma, however, relied on the platelets as a source of phospholipid to the extent that variables such as centrifugation and patient platelet count had a significant bearing on the test results. The partial thromboplastin time (PTT) introduces a platelet substitute that eliminates test variability due to the availability of platelet phospholipid. By adding a substance to activate factors XII and Xl, the contact factors, the partial thromboplastin time becomes the "activated" partial thromboplastin time (APTT). Because coagulation endpoints are shorter and sharper than with the PTT, the APTT has proven to be a simple and highly reliable measurement of the intrinsic coagulation mechanism.

Laboratory monitoring of heparin therapy is desirable to ensure that an appropriate antithrombotic effect is obtained, while guarding against bleeding complications of an overdosage. Currently, the APTT is the most common test used to monitor heparin therapy. Monitoring by APTT evaluates heparin's overall activity throughout the entire coagulation system i.e., inactivation of thrombin, Xa, Xlla, Xla, and IXa. Heparin treatment is usually monitored to maintain the ratio of the patient's APTT to the mean control APTT within a defined range of approximately 1.5 to 2.5, referred to as the therapeutic range. Laboratory and clinical studies have established a therapeutic range that is equivalent to a heparin level of 0.2 to 0.4 Upper milliliter (mL) by protamine titration, or 0.35 to 0.7 Upper mL according to the level of anti-Xa activity. It should be noted that the responsiveness of the reagents used in APTT tests can vary widely. The therapeutic range for any given APTT reagent should therefore be established in the clinical laboratory to correspond to a heparin level of 0.2 to 0.4 U/mL by protamine titration.

Alternative Coagulation Assays to PTT

Anti-Xa Assay: An alternative approach is to assay for heparin exploiting its catalysis by antithrombin 111 inhibition of coagulation enzymes, particularly factor Xa. The factor Xa inhibition test (anti-Xa assay) is the most useful test for assaying the widest variety of therapeutic heparin preparations. In this method, both factor Xa and antithrombin 111 are present in excess and the residual factor Xa activity is inversely proportional to the heparin concentration. The assumption is made that the patient has a normal concentration of antithrombin III. (For a patient with ATIII deficiency a heparin concentration is measured, but this does not necessarily correspond to the anticoagulant capacity in vivo.) It is recommended to also measure the antithrombin 111 level for all patients under heparin therapy when using this type of assay to ensure normal ATIII activity. The therapeutic range of the anti-Xa assay in the treatment of thromboembolic disease established by laboratory and clinical studies for unfractionated heparin is 0.35 to 0.7 anti-Xa Units/mL. The therapeutic range for LMW heparins has not been well established at this time.

There are several clinical situations where the specific measurement of heparin levels using the anti-factor Xa method may be necessary. Patients receiving heparin but demonstrating an inadequate APTT response can be evaluated for heparin by the anti-Xa assay. Monitoring of heparin is difficult by conventional methods when the baseline APTT is prolonged as seen in patients with lupus anticoagulants and deficiencies of factor XII (Hagemen factor), prekallikrein (Fletcher factor), and high molecular weight kininogen (Fitzgerald factor). A quantitative anti-Xa assay makes heparin monitoring possible in these clinical situations.

Sensing Cardiac Function

A number of means are available for assessing cardiac function. An ultrasound echocardiogram can non-invasively assess a number of parameters of the heart, such as left ventricle size and cardiac output. An electrocardiogram (ECG) may be recorded non-invasively or invasively, and may be used to detect or diagnose a number of cardiac conditions, e.g., ischemia, arrhythmia, etc. Invasive pressure transducers may be used to determine left ventricular end diastolic pressure, pulmonary capillary wedge pressure, and systemic blood pressure. For instance, a thermal dilution catheter, the dye-dilution method, and/or catheter pressure transducers/catheter tip transducers may be used to measure blood pressure or cardiac output. Cardiac output, the total volume of blood pumped by the ventricle per minute, is the product of heart rate and stoke volume.

In a 1990 study of 21 heart transplant patients, Pepke-Zaba, et al. compared cardiac output measured by thermodilution and by impedance cardiography. They found close agreement between the measurements, both at rest and during exercise. Both measurements followed changes in heart rate and oxygen consumption. Both thermodilution and impedance cardiography methods elicited good reproducibility of cardiac output measurements at rest and during exercise. The authors concluded that the noninvasive and continuous record of cardiac output obtained by impedance cardiography can be used for the monitoring of cardiac output. [Pepke-Zaba, et al. "Validation of impedance cardiography measurements of cardiac output during limited exercise in heart transplant recipients" Transplant International, 1990 July;3(2):108-12.]

As should be understood by the foregoing, given the prevalence of thromboembolic disease, alternative treatments and improvements in monitoring, preventing, and treating thromboembolic disease are needed. For instance, a closed-loop system would allow automatic or semi-automatic adjustment of treatment and would allow tighter control of clotting than possible with conventional periodic tests of clotting parameters.

SUMMARY

Method and systems of treating a patient with at least one of a myocardial infarction, a stroke, and a pulmonary embolism include providing a stimulator coupled to at least one electrode and a catheter, configuring one or more stimulation parameters to treat at least one of a myocardial infarction, a stroke, and a pulmonary embolism, programming the stimulator with the one or more stimulation parameters, delivering with the stimulator via the catheter at least one drug to at least one tissue in accordance with the one or more stimulation parameters, and limiting perfusion of the at least one tissue by delivering electrical stimulation with the stimulator via the at least one electrode to the at least one tissue. The at least one drug is configured to provide at least one of thrombolytic and anticoagulation treatment to the at least one tissue and the electrical stimulation is configured to constrict at least one arteriole supplying the at least one tissue.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Figure 1A:
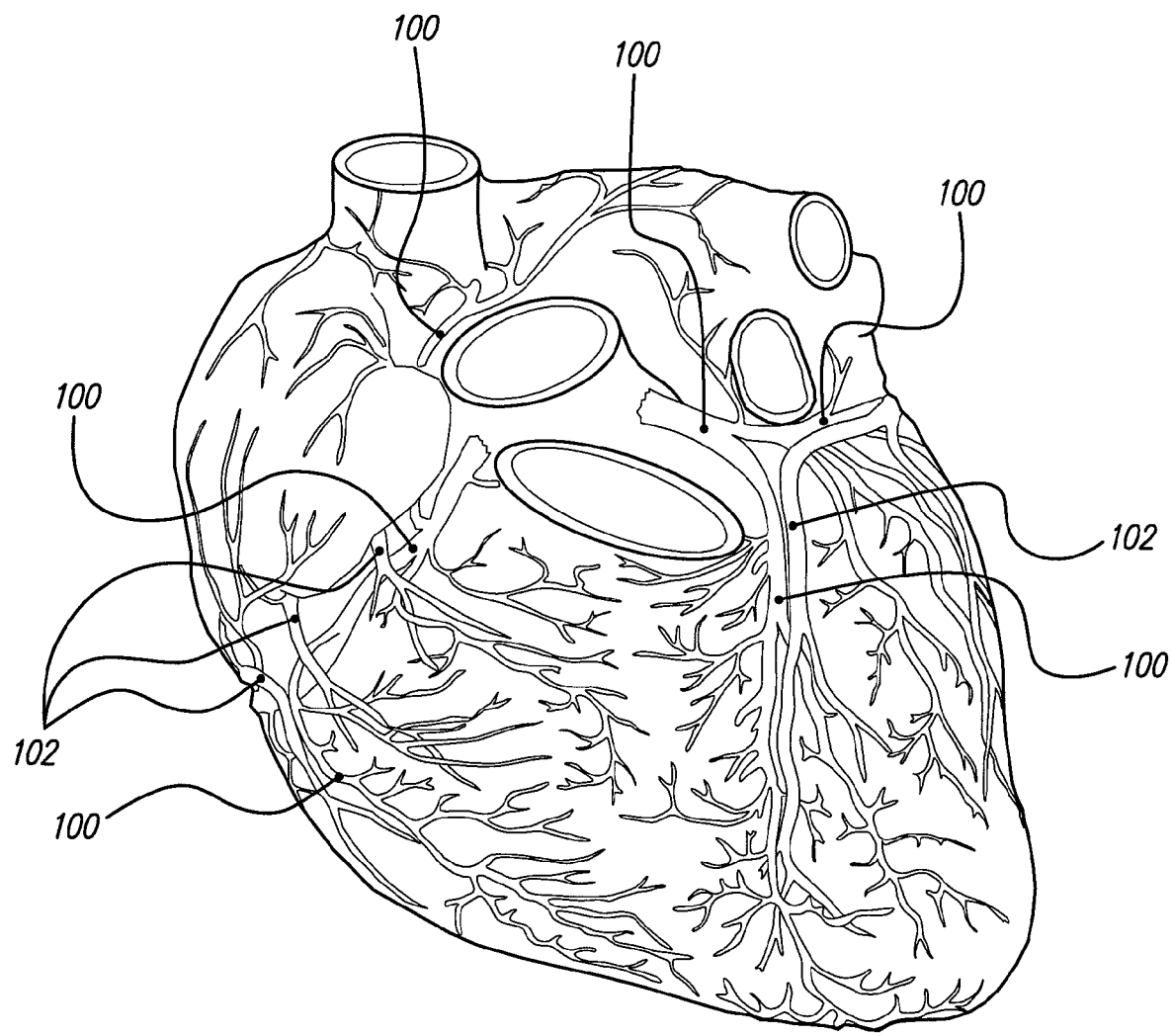
FIG. 1A is a view of the sternocostal surface of the heart.

Described herein are systems and methods for treating a patient with at least one of a myocardial infarction, a stroke, and a pulmonary embolism. The present systems and methods achieve unprecedented levels of treatment by combining administration of acute (on-demand) and traditional chronic (basal or periodic bolus) treatment and prevention of thromboembolic disease. Additionally, the present systems and methods optionally combine electrical stimulation with delivery of one or more drugs for acute and/or chronic treatment. In addition, some embodiments include monitoring of anticoagulation status to achieve an unprecedented level of treatment of thromboembolic disease.

Anticoagulation therapy may be carried out by delivery of one or more known drugs or other substances known to decrease coagulability. Such drugs may include any and all forms of heparin, including low molecular weight heparin derivatives. Such drugs may also include any form of warfarin. Such drugs may also include any form of aspirin or any other substance known to inhibit platelet aggregation, such as clopidogrel and ticlopidine. Such substances may also include antibodies to any clotting factors or other enzymes or substances believed to be involved in the clotting process, such as those mentioned herein.

In some examples, anticoagulation therapy is carried out chronically through a basal rate and/or periodic bolus delivery of an anticoagulant(s). The parameters of delivery may be constant or may be modulated by a clinician, other caregiver, or the patient. The parameters of delivery may also be modulated by sensed data or by another device(s), as discussed herein.

In other examples, delivery of an anticoagulant(s) may be increased during an acute emergency, e.g., myocardial infarction, stroke (a.k.a., cerebrovascular accident, or CVA), evolving deep vein thrombosis, and the like. Such an increase may reflect an increase in basal rate and/or an increase in bolus dose and/or rate. This increase in delivery may be initiated by a clinician, other caregiver, or the patient. This increase in delivery may additionally or alternatively be initiated by sensed data or by another device(s), as discussed herein.

In yet other examples, delivery of a thrombolytic(s) may be triggered during an acute emergency, e.g., myocardial infarction, stroke, evolving deep vein thrombosis, and the like. Such delivery may be achieved through a basal rate and/or periodic bolus delivery of a thrombolytic(s). This delivery may be initiated by a clinician, other caregiver, or the patient. This delivery may additionally or alternatively be initiated by sensed data or by another device(s), as discussed herein.

The stimulator used with the present systems and methods possesses one or more of the following properties, potentially among others:

- at least one pump and at least one catheter for delivering a drug or drugs to surrounding tissue and, optionally, at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the stimulator; and
- a form factor making the stimulator implantable in a target area in the body.

A stimulator may operate independently, or in a coordinated manner with other implanted stimulators, other implanted devices, and/or with devices external to a patient's body. For instance, a stimulator may incorporate means of sensing thromboembolic disease, cardiac ischemia, cerebral ischemia, pulmonary ischemia, limb ischemia, mesenteric ischemia, myocardial infarction, stroke, pulmonary embolism, deep vein thrombosis, one or more symptoms of any of these, and/or the coagulation state of the patient. Sensed information may be used to control the drug and/or electrical stimulation parameters of the stimulator in a closed loop manner. The sensing and stimulating means may be incorporated into a single stimulator, or a sensing means may communicate sensed information to at least one stimulator with stimulating means.

For most patients, a continuous or intermittent stimulation throughout the day is needed to provide an adequate amount of treatment. These patients may best utilize a stimulator that has a self-contained power source sufficient to deliver repeated pulses for at least several days and that can be recharged repeatedly, if necessary. In some examples, the use of a stimulator with a rechargeable battery thus provides these patients the portability needed to free the patient from reliance on RF power delivery. Alternatively, the power source may be a primary battery that may last several years.

For purposes of this patent application, it is sufficient to note that RF controlled stimulators receive power and control signals from an extra corporeal antenna coil via inductive coupling of a modulated RF field. Battery-operated stimulators incorporate a power source within the device itself but rely on RF control, inductive linking, or the like to program stimulus sequences and, if a rechargeable/replenishable power source is used, to recharge/replenish the power source, when needed. In some examples, each implanted stimulator may be commanded to produce an electrical and/or infusion pulse of a prescribed magnitude and duration and at a repetition rate sufficient to treat the targeted tissue.

For instance, program delivery may be directed with commands from a patient-governed control switch or controller, which may be handheld, containing a microprocessor and appropriate nonvolatile memory, such as electronically erasable programmable read-only-memory (EEPROM). The controller may control the implantable stimulator by any of various means. For instance, the stimulator may sense the proximity of a permanent magnet located in the controller, or may sense RF transmissions from the controller. However, it will be evident to those of skill in circuitry and computing that many different system architectures and components could be used to achieve similar functionality with either a battery-powered or RF-powered stimulator.

Figure 1B:
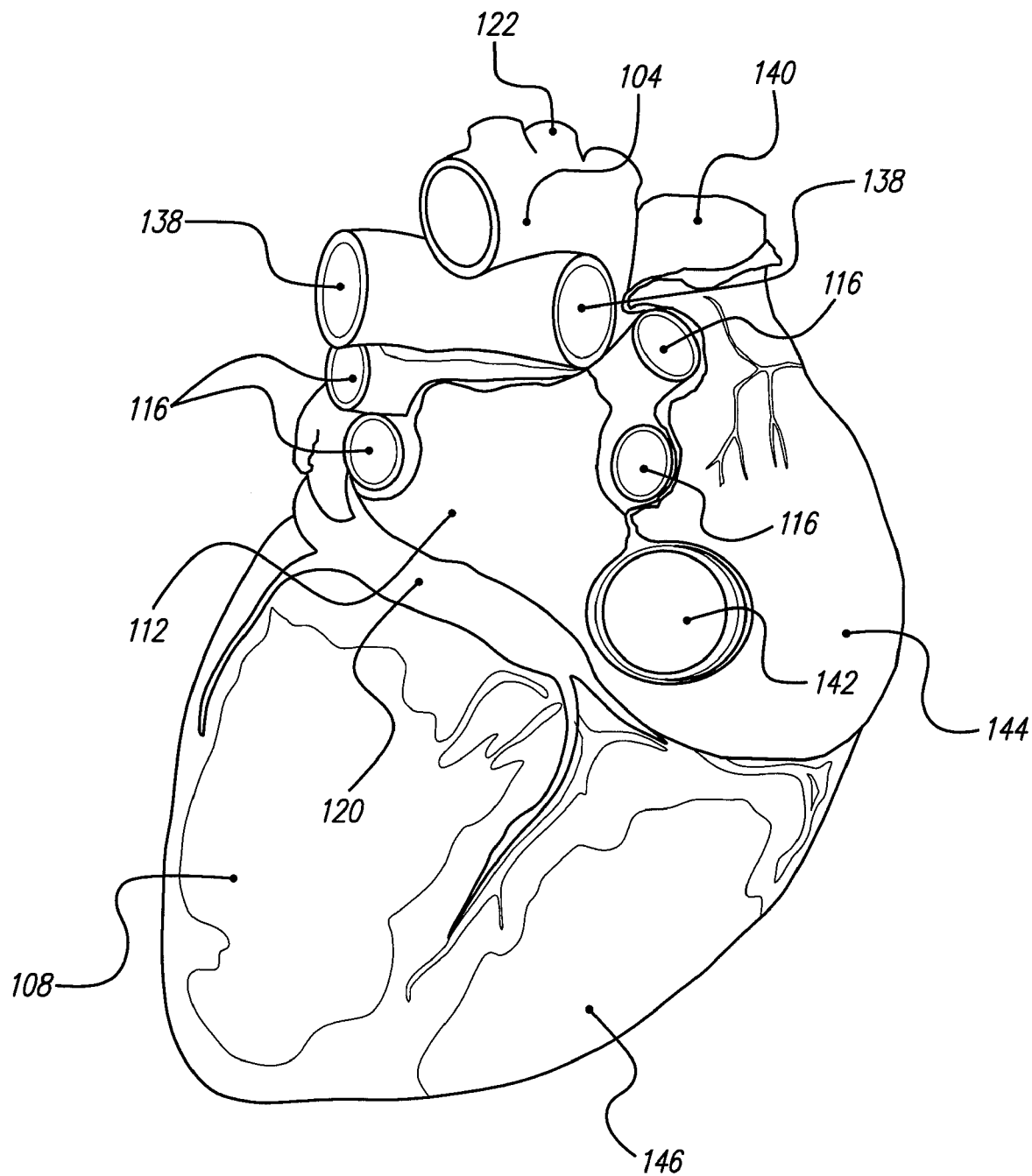
FIG. 1B is a posteroinferior view of the diaphragmatic surface of the heart.
Figure 2:
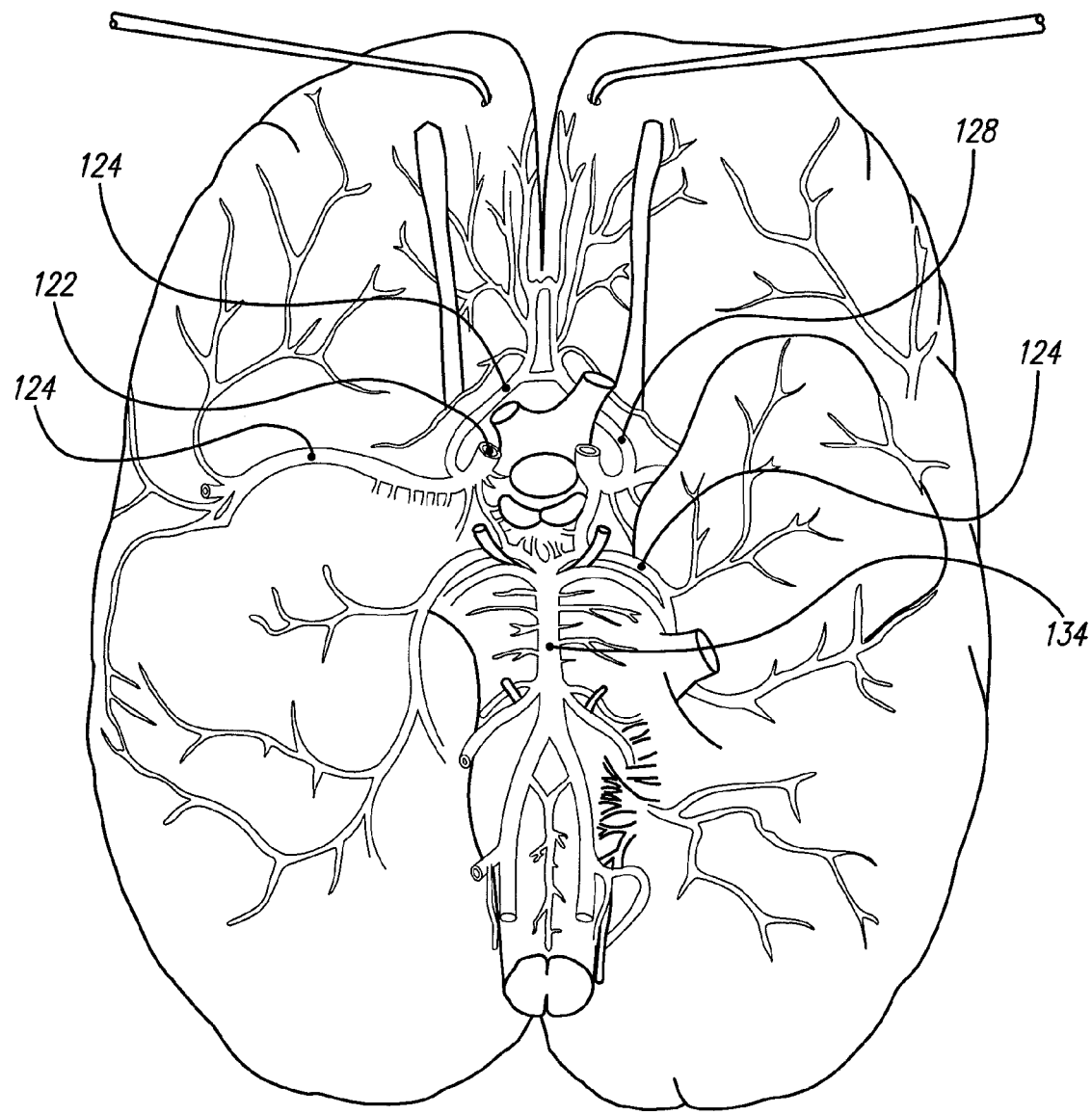
FIG. 2 is an inferior view of the arteries of the brain.

FIG. 1A depicts the coronary arteries and the cardiac veins of the sternocostal surface of the heart, while FIG. 1B is a posteroinferior view of the diaphragmatic surface of the heart, and FIG. 2 shows an inferior view of the arteries of the brain. As mentioned earlier, delivery of one or more stimulating drugs may be used to prevent or treat thromboembolic disease. Electrical stimulation may also be applied during infusion of a stimulating drug(s).

The drug(s) may be delivered to any vessel that may influence the coronary circulation, including one or more of the coronary arteries 100 (which herein describes also branches of the coronary arteries), one or more of the coronary veins 102 (also including branches), the aorta 104, the left ventricle 108, the left atrium 112, one or more of the pulmonary veins 116, and/or the coronary sinus 120. Such application is most appropriate for, but not limited to, patients with cardiac disease, e.g., history of myocardial infarction, coronary artery disease, or atrial fibrillation.

The drug(s) are additionally or alternatively delivered to any vessel that may influence the cerebral circulation, including any of the carotid arteries 122 (FIG. 1B shows the left common carotid artery and FIG. 2 shows the internal carotid artery), the aorta 104, any of the anterior, middle, or posterior cerebral arteries 124, the circle of Willis 128, any of meningeal arteries (not shown), and/or the basilar artery 134. Such application is most appropriate for, but not limited to, patients with history of or with risk factors for stroke.

The drug(s) are additionally or alternatively delivered to any vessel that may influence the pulmonary circulation, including any of the pulmonary arteries 138, the superior vena cava 140, the inferior vena cava 142, the right atrium 144, and the right ventricle 146. Such application is most appropriate for, but not limited to, patients with history of pulmonary embolism (PE) or with risk factors for PE.

The drug(s) are additionally or alternatively delivered to any vessel that may influence the circulation of the lower limbs, including any of the deep veins of the leg (not shown), any of the ilio-femoral vessels (not shown, e.g., common iliac vessel, internal iliac vessel, external iliac vessel, femoral vessel), and calf veins (not shown). Such application is most appropriate for, but not limited to, patients with history of deep vein thrombosis (DVT) or with risk factors for DVT.

The drug(s) are additionally or alternatively delivered to any vessel that may influence the circulation of the intestinal or other visceral organs, including any of the mesenteric vessels, renal vessels, celiac trunk, and middle colic artery (none shown). Such application is most appropriate for, but not limited to, patients with history of or with risk factors for mesenteric ischemia.

Target sites for drug infusion may additionally or alternatively include any other blood vessel, as anticoagulation therapy is typically delivered systemically. Thrombolytic therapy is ideally but not necessarily targeted to an occluded vessel, in order to avoid systemic side effects. A blood vessel that is unlikely to suffer significant trauma with implantation or attachment of a chronic infusion catheter (e.g., the inferior vena cava 142) may be used in the case of systemic therapy. As used herein, reference to any vessel refers also to the branches of the vessel.

As indicated above, the systems and methods described herein are directed to preventing and treating thromboembolytic disease and relieving its symptoms. In some examples, one or more stimulating drugs, possibly combined with electrical stimulation, are applied to one or more of the above mentioned areas for such treatment. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

As used herein, stimulating drugs comprise medications and other pharmaceutical compounds, anesthetic agents, synthetic or natural hormones, neurotransmitters, interleukins, cytokines, lymphokines, chemokines, growth factors, and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

According to some examples, an implantable pump and catheter(s) are used to deliver one or more stimulating drugs, plus, optionally, an implantable signal generator and electrode(s) may also deliver electrical stimulation to the target area(s). One or more catheters are surgically implanted to infuse the stimulating drug(s), and, optionally, electrode(s) on a lead(s) are implanted to provide electrical stimulation.

In some examples, at least one stimulator may be provided. In the case of drug infusion only, an exemplary stimulator comprises an implantable pump. In the case of electrical stimulation, as well, an exemplary stimulator also comprises an implantable pulse/signal generator (IPG). In cases where both electrical stimulation and drug infusion are required or desired, more than one stimulators may be used. Alternatively, a stimulator may provide both electrical stimulation and one or more stimulating drugs.

In some examples, the stimulator that may be implanted in a surgically-created shallow depression or opening, e.g., in the thorax, abdomen, or above the buttock. The stimulator may conform to the profile of surrounding tissue and/or bone, and is compact. This may minimize any cosmetic impact, and minimize pressure applied to the skin, which pressure can result in skin erosion or infection. As such, the stimulator may have a diameter of about 75 mm, or only about 65 mm, or even less than about 55 mm. In these configurations, stimulator thickness may be approximately 10-12 mm, or even less than about 10 mm.

Figure 3:
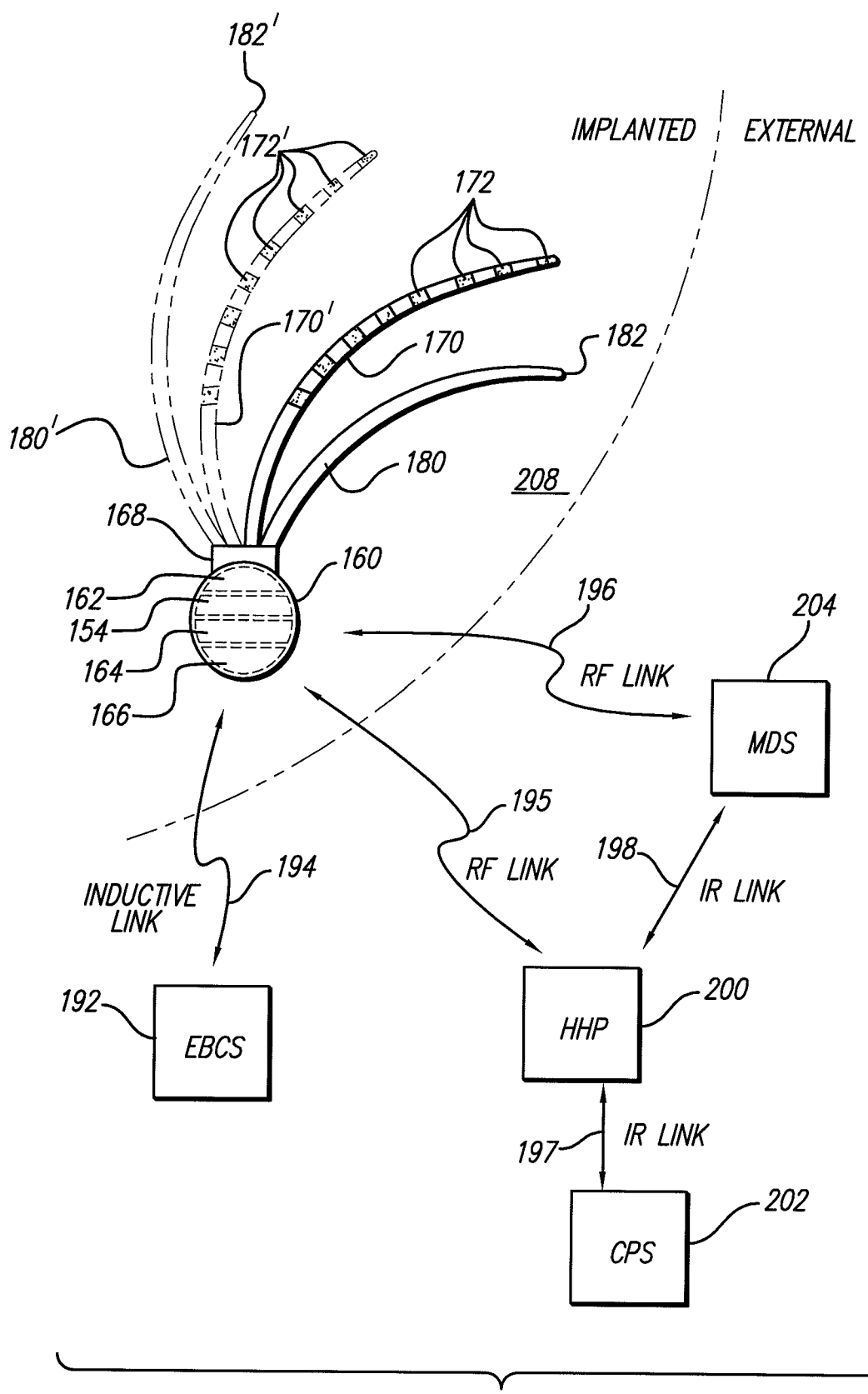
FIG. 3 illustrates an exemplary embodiment of a stimulation system.

In one embodiment seen in FIG. 3, one or more catheters 180 and, optionally, one or more leads 170 attach to stimulator 160 and run subcutaneously, such as in a surgically-created tunnel(s), to the tissues to be stimulated. In the case of treatment including electrical stimulation, one or more electrodes 172 are carried on lead 170 having a proximal end coupled to stimulator 160. Electrode(s) 172 may include, for instance, a tip electrode and/or one or more ring electrodes, allowing, e.g., temporally synchronized stimulation. The lead contains wires electrically connecting electrodes 172 to stimulator 160. Stimulator 160 contains electrical components 154 that produce electrical stimulation pulses that travel through the wires of lead 170 and are delivered to electrode(s) 172, and thus to the tissue surrounding electrode(s) 172. Implantation of such stimulators, leads, and catheters in the locations specified herein is performed as known to those in the art, e.g., as known to interventional cardiologists.

In the case of treatment alternatively or additionally constituting drug infusion, catheter(s) 180 are coupled at a proximal end to stimulator 160, which contains at least one pump 162 for storing and dispensing one or more drug(s) through the catheter(s) 180. At or along a distal end, catheter 180 has at least one discharge portion 182 for infusing dosages of one or more drugs into a predetermined site. Catheter 180 may also act as a lead, additionally including electrode(s) 172 at and/or along its distal end.

To protect the components inside stimulator 160, some or all of the case of the stimulator may be hermetically sealed. For additional protection against, e.g., impact, the case may be made of metal (e.g. titanium), ceramic, or the like, which materials are also, advantageously, biocompatible. The material comprising the case of the stimulator 160 may be chosen to limit passage of water vapor, while permitting passage of electromagnetic fields used to transmit data and/or power. In addition, stimulator 160 may be configured to be Magnetic Resonance Imaging (MRI) compatible.

According to embodiments as depicted in FIG. 3, at least one lead 170 and/or catheter 180 is attached to stimulator 160, via a suitable connector(s) 168, if necessary. Each lead includes at least one electrode 172, and may include as many as sixteen or more electrodes 172. As known in the art, the case of stimulator 160 (a.k.a. the can) may act as an indifferent electrode for monopolar stimulation. Additional leads 170' and/or catheter(s) 180' may be attached to stimulator 160. Hence, FIG. 3 shows (in phantom lines) a second catheter 180', having discharge portion 182', and a second lead 170', having electrodes 172' thereon, also attached to stimulator 160.

Lead(s) 170/170' may, for instance, be less than about 5 mm in diameter, or may be even less than about 1.5 mm in diameter. Electrodes 172, 172' may be made of a noble or refractory metal or compound, such as platinum, iridium, tantalum, titanium, titanium nitride, niobium, or alloys of any of these, in order to avoid corrosion or electrolysis which could damage the surrounding tissues and/or the device. In certain embodiments, stimulator 160 is programmable to produce monopolar electrical stimulation, e.g., using the stimulator case as an indifferent electrode, or bipolar electrical stimulation, e.g., using one of the electrodes of the electrode array as an indifferent electrode. For instance, stimulator 160 may have at least four channels and may drive up to sixteen electrodes or more.

Stimulator 160 (which herein refers to implantable pump stimulators, IPG/pump combination stimulators, and/or other alternative devices known in the art) contains, when necessary and/or desired, electrical circuitry 154 (FIG. 3) for receiving data and/or power from outside the body by inductive, radio frequency (RF), or other electromagnetic coupling. In some embodiments, electrical circuitry 154 includes an inductive coil for receiving and transmitting RF data and/or power, an integrated circuit (IC) chip for decoding and storing stimulation parameters and generating stimulation pulses (either intermittent or continuous), and additional discrete components required to complete the circuit functions, e.g., capacitor(s), resistor(s), coil(s), and the like. Circuitry 154 may dictate, for instance, the amplitude and duration of the electrical current pulse, when electrical stimulation is used.

Stimulator 160 may also advantageously include a programmable memory 164 for storing set(s) of data, stimulation, and control parameters. Among other things, memory 164 may allow electrical and/or drug stimulation and/or control parameters to be adjusted to settings that are safe and efficacious with minimal discomfort for each individual. Specific parameters may provide therapeutic advantages for various types and degrees of thromboembolic disease. For instance, some patients may respond favorably to intermittent stimulation, while others may require continuous stimulation for treatment and relief. Different medications, infusion parameters, and/or electrical stimulation parameters may have different effects on anticoagulation and thrombolysis. In some embodiments, electrical and drug stimulation parameters are controlled independently, e.g., continuous drug stimulation and no electrical stimulation. However, in some instances, they are advantageously coupled, e.g., electrical stimulation may be programmed to occur only during drug infusion.

Electrical stimulation may be applied as for cardiac pacing and/or cardiac defibrillation. Such stimulation is commonly performed by implantable devices referred to as cardiac pacemakers (used to treat cardiac arrhythmias or other cardiac disease) and implantable cardiac defibrillators (ICDs, used to treat cardiac fibrillation), respectively. Modern ICDs perform both the pacing and defibrillating functions. Operation of these devices, including stimulation parameters, are well-known to those skilled in the art.

In addition, different parameters may have different effects on different tissue. Therefore, stimulation and control parameters may be chosen to target specific neural, muscular, and/or other cell populations and to exclude others, or to increase activity in specific neural, muscular, and/or other cell populations and to decrease activity in others. For example, relatively low frequency neurostimulation (i.e., less than about 50-100 Hz) typically has an excitatory effect on surrounding neural tissue, leading to increased neural activity, whereas relatively high frequency neurostimulation (i.e., greater than about 50-100 Hz) typically has an inhibitory effect, leading to decreased neural activity.

Similarly, excitatory neurotransmitters (e.g., acetylcholine), agonists thereof, and agents that act to increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof (e.g., benzodiazepines such as lorazepam and diazepam), and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity.

In some embodiments, stimulation of nerves and/or smooth muscle is advantageously used to modulate or direct the flow of anticoagulation medication. For example, stimulation of arteriolar smooth muscle tissue and/or the excitatory nerves innervating this tissue (sympathetic nerves) leads to a decrease of perfusion of the tissue fed by such arterioles due to a constriction in lumen area caused by contraction of the surrounding smooth muscle. Such a decrease in perfusion would allow a medication to remain in a tissue longer, if such medication were delivered to the tissues fed by constricted arterioles. Alternatively, such a decrease in perfusion may be used to selectively decrease delivery of a medication if the medication were delivered systemically and arterioles in a certain region were constricted. Relatively low frequency electrical stimulation (less than about 50-100 Hz) is likely to cause contraction of arteriolar smooth muscle, as are alpha-adrenoceptor agonists (e.g., phenylephrine, norepinephrine). Conversely, alpha-adrenoceptor antagonists (e.g., prazosin, terzosin, phentolamine) are likely to cause relaxation and dilation of vascular smooth muscle.

Some embodiments of stimulator 160 also include a power source and/or power storage device 166 (FIG. 3). Possible power options for an exemplary stimulation device, described in more detail below, include but are not limited to an external power source coupled to the stimulation device (e.g., via an RF link), a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as depicted in FIG. 3, stimulator 160 includes a rechargeable battery as a power source/storage device 166. The battery is recharged, as required, from an external battery charging system (EBCS) 192, typically through an inductive link 194. In these embodiments, stimulator 160 includes a processor and other circuitry 154 that allow it to generate electrical/infusion pulses that are applied to a patient 208 through electrodes 172 and/or catheter(s) 180 in accordance with a program and stimulation parameters stored in programmable memory 164. As stated earlier, stimulation pulses of drugs include various types and/or rates of infusion, such as intermittent infusion, infusion at a constant rate, and bolus infusion.

According to certain embodiments, a stimulator operates independently. According to other embodiments, a stimulator operates in a coordinated manner with other stimulator(s), other implanted device(s), and/or other device(s) external to the patient's body. For instance, a stimulator may control or operate under the control of another implanted stimulator(s), other implanted device(s), and/or other device(s) external to the patient's body. A stimulator may communicate with other implanted stimulators, other implanted devices, and/or devices external to a patient's body via, e.g., an RF link, an ultrasonic link, a thermal link, and/or an optical link. Specifically, a stimulator may communicate with an external remote control (e.g., patient and/or clinician programmer) that is capable of sending commands and/or data to a stimulator and that may also be capable of receiving commands and/or data from a stimulator.

For example, in embodiments such as shown in FIG. 3, stimulator 160 may be activated and deactivated, programmed and tested through a hand held programmer (HHP) 200 (which may also be referred to as a patient programmer and may, but not necessarily, be hand held), a clinician programming system (CPS) 202 (which may also be hand held), and/or a manufacturing and diagnostic system (MDS) 204 (which may also be hand held). HHP 200 may be coupled to stimulator 160 via an RF link 195. Similarly, MDS 204 may be coupled to stimulator 160 via another RF link 196. In a like manner, CPS 202 may be coupled to HHP 200 via an infra-red link 197; and MDS 204 may be coupled to HHP 200 via another infra-red link 198. Telecommunicative links other than RF or infra-red may also be used for these purposes. Through these links, CPS 202, for example, may be coupled through HHP 200 to stimulator 160 for programming or diagnostic purposes. MDS 204 may also be coupled to stimulator 160, either directly through RF link 196, or indirectly through IR link 198, HHP 200, and RF link 195.

Figure 4:
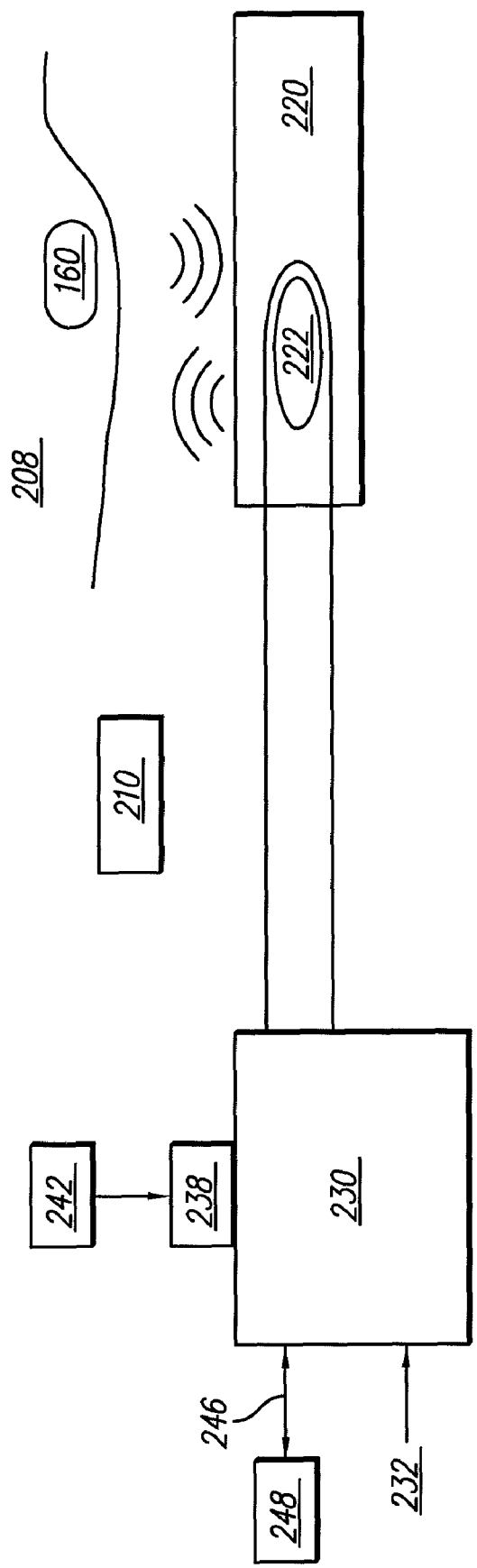
FIG. 4 illustrates an additional exemplary embodiment of the stimulation system.

In certain embodiments, and as illustrated in FIG. 4, the patient 208 may switch stimulator 160 on and off by use of controller 210, which may be handheld. Stimulator 160 is operated by controller 210 by any of various means, including sensing the proximity of a permanent magnet located in controller 210, sensing RF transmissions from controller 210, or the like.

Additional and alternative exemplary external components for programming and/or providing power to stimulator 160 are also illustrated in FIG. 4. When communication with stimulator 160 is desired, patient 208 is positioned on or near external appliance 220, which appliance contains one or more inductive coils 222 or other means of communication (e.g., RF transmitter and receiver). External appliance 220 is connected to or is a part of external circuitry appliance 230 which may receive power 232 from a conventional power source. External appliance 230 contains manual input means 238, e.g., a keypad, whereby the patient 208 or a caregiver 242 may request changes in the electrical and/or drug stimulation parameters produced during the normal operation of stimulator 160. In these embodiments, manual input means 238 include various electromechanical switches and/or visual display devices that provide the patient and/or caregiver with information about the status and prior programming of stimulator 160.

Alternatively or additionally, external appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

One or more of the external appliance(s) may be embedded in a cushion, mattress cover, garment, or the like. Other possibilities exist, including a strap, patch, or other structure(s) that may be affixed to the patient's body or clothing. External appliances may include a package that can be, e.g., worn on the belt, may include an extension to a transmission coil affixed, e.g., with a VELCRO® band or an adhesive, or may be combinations of these or other structures able to perform the functions described herein.

To help determine the amount and/or type(s) of stimulating drug(s), and optionally, the strength and/or duration of electrical stimulation, required to produce the desired therapeutic effect, in some embodiments, a patient's response to and/or need for treatment is sensed. For instance, the electrical activity produced in response to stimulation may be detected, e.g., via recording of the associated electrocardiogram (ECG). When catheters and/or electrodes of a stimulator are implanted, for example, in and/or adjacent the left coronary artery or its branches, signals from an ECG sensor built into the stimulator may be used to adjust stimulation parameters. (As used herein, "adjacent" or "near" means as close as reasonably possible to target tissue(s), including touching or even being positioned within the tissue, but in general, may be as far as can be reached with the stimulation pulses). ECG and/or other sensing may be performed by an internal or external device. For instance, beat-to-beat T-wave variations, which are abnormal ECG events associated with an increased likelihood of ventricular arrhythmia, may be detected with measurement and comparisons of T-waves at a microvolt level (for instance, by the Heartwave™ System available from Cambridge Heart, Inc. of Bedford, Mass., which performs a Microvolt T-Wave Alternans™ Test).

Alternatively, a "stimulator" dedicated to sensory processes communicates with a stimulator that provides the electrical and/or infusion pulses. For instance, a microstimulator, such as a BION® manufactured by Advanced Bionics of Sylmar, Calif., may be used to detect abnormal cardiac electrocardiogram (ECG) changes/events. For instance, a BION® may use one of many algorithms for analyzing ECGs. These algorithms can operate in the frequency domain, time domain or both. They may employ linear, non-linear, or statistical analysis to categorize the electrogram as originating from various modes, i.e., normal sinus rhythms, sinus tachycardia, ventricular tachycardia, and ventricular fibrillation. In addition, by finding the p, R, and T waves or analyzing the timing of the relationships and durations of the p-wave, QRS complex, and T-wave, it is possible to identify various abnormal events and disease states, and make predictive diagnosis about perfusion of the myocardium. See, for instance, U.S. Pat. No. 5,513,644, titled "Cardiac arrhythmia detection system for an implantable stimulation device," which is incorporated herein by reference in its entirety.

Alternatively or additionally, a "stimulator" (which may be a microstimulator, and which may or may not have "stimulating" means) may incorporate means of sensing the coagulation state of the patient, e.g., via Prothrombin Time (PT), International Normalized Ratio (INR), Partial Thromboplastin Time (PTT), Specific Prothrombin (Factor II) Assay, Native Prothrombin Antigen Assay, and/or Anti-Xa Assay. In other examples, a microstimulator(s) may sense EEG changes/events, or other indicator(s) of myocardial infarction, stroke, pulmonary embolism, deep vein thrombosis, and/or symptoms thereof. Alternatively or additionally, a "stimulator" may incorporate means of sensing thromboembolic disease, cardiac ischemia, cerebral ischemia, and/or pulmonary ischemia, limb ischemia, e.g., via an oxygen sensor or a flow sensor in one or more of these tissues. For instance, a microstimulator(s) may sense Troponin-I or Troponin-T, which are marker of ischemia. See, for instance, U.S. Pat. No. 5,753,517, titled "Quantitative immunochromatographic assays," which is incorporated herein by reference in its entirety. Antibodies that bind to Troponin-I may be sensed, for instance, with a detection reagent (to which the antibodies bind) and measured using electrical conductivity or capacitance. A microstimulator or other sensor could additionally or alternatively measure an antibody that fluoresces when binding to Troponin-I, for instance, with an LED encased in a hermetic glass seal coated with the antibody.

As described below, implant circuitry 154 may, if necessary, amplify and transmit these sensed signals, which may be analog or digital. A stimulator may incorporate other means of sensing in order to determine the required stimulation, including sensing levels or changes of any blood borne substance, including medications, hormones, or other substances, such as D-dimers, and/or other methods mentioned herein, and yet others evident to those of skill in the art upon review of the present disclosure. For instance, one or more Chemically Sensitive Field-Effect Transistors (CHEM-FETs), such as Enzyme-Selective Field-Effect Transistors (ENFETs) or Ion-Sensitive Field-Effect Transistors (ISFETs, as are available from Sentron CMT of Enschede, The Netherlands), may be used. The sensed information may be used to control stimulation parameters in a closed-loop manner.

Therefore, in several embodiments, a first and second "stimulator" are provided. The second "stimulator" periodically (e.g., once per minute) senses, for example, the level of heparin in the circulatory system via an anti-Xa assay, and transmits this information to the first stimulator. The first stimulator uses the sensed information to adjust drug and/or electrical stimulation parameters according to an algorithm programmed, e.g., by a clinician. For example, the infusion rate of an anticoagulant, such as heparin may be increased in response to decreased anti-Xa activity. In some alternatives, one stimulator performs both the sensing and stimulating functions.

While a stimulator may also incorporate means of sensing thromboembolic disease, cardiac ischemia, cerebral ischemia, pulmonary ischemia, myocardial infarction, stroke, pulmonary embolism, deep vein thrombosis, the coagulation state of a patient, and/or symptoms of any of these, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted stimulator(s) 160. However, in some cases, it may not be necessary or desirable to include a sensing function or device, in which case stimulation parameters are determined and refined, for instance, by patient feedback, or the like.

Thus, one or more external appliances may be provided to interact with stimulator(s) 160, and may be used to accomplish, potentially among other things, one or more of the following functions:

Function 1: If necessary, transmit electrical power from the external electronic appliance 230 via appliance 220 to stimulator 160 in order to power the device and/or recharge the power source/storage device 166. External electronic appliance 230 may include an automatic algorithm that adjusts drug and/or electrical stimulation parameters automatically whenever the stimulator(s) 160 is/are recharged.

Function 2: Transmit data from the external appliance 230 via the external appliance 220 to stimulator 160 in order to change the parameters of drug and/or electrical stimulation used by stimulator 160.

Function 3: Transmit sensed data indicating a need for treatment or in response to stimulation from stimulator 160 to external appliance 230 via external appliance 220.

Function 4: Transmit data indicating state of the stimulator 160 (e.g., battery level, drug level, electrical stimulation and/or infusion settings, etc.) to external appliance 230 via external appliance 220.

By way of example, referring for example to FIG. 4, a treatment modality for thromboembolic disease may be carried out according to the following procedure:

1. A stimulator 160 is implanted so that its catheter discharge portion 182 and one or more electrodes 172 are located in the coronary arteries, sinus, and/or veins. If necessary or desired, additional leads 170' and/or catheters 180' may be used so that, for example, electrodes 172' and/or catheter discharge portions(s) 182' may additionally or alternatively be located in or adjacent atria, ventricles, blood vessels, or on the surface of the myocardium.

2. Using Function 2 described above (i.e., transmitting data) of external electronic appliance 230 and external appliance 220, the stimulator 160 is commanded to infuse amounts of heparin, possibly while producing a series of excitatory electrical stimulation pulses.

3. After each electrical/infusion pulse, series of stimulation pulses, or at some other predefined interval, any change in, e.g., anti-Xa activity or activated partial thromboplastin time (APTT) resulting from the stimulation is sensed, for instance, by one or more electrodes 172 and/or 172' acting as sensors. If necessary, these responses are converted to data and telemetered out to external electronic appliance 230 via Function 3.

4. From the response data received at external appliance 230, or from other assessment, the stimulus threshold for obtaining a response is determined and is used by a clinician 242 acting directly 238 or by other computing means 248 to transmit the desired electrical and/or drug stimulation parameters to stimulator 160 in accordance with Function 2. Alternatively, external appliance 230 makes the proper adjustments automatically, and transmits the proper stimulation parameters to stimulator 160. In yet another alternative, stimulator 160 adjusts stimulation parameters automatically based on the sensed response.

5. When patient 208 desires to invoke electrical stimulation and/or drug infusion, patient 208 employs controller 210 to set stimulator 160 in a state where it delivers a prescribed stimulation pattern from a predetermined range of allowable stimulation patterns.

6. Patient 208 employs controller 210 to turn off stimulator 160, if desired.

7. Periodically, the patient or caregiver recharges the power source/storage device 166 of stimulator 160, if necessary, in accordance with Function 1 described above (i.e., transmit electrical power).

For the treatment of any of the various types and severities of thromboembolic disease, symptoms thereof, and/or various coagulation states of patients, it may be desirable to modify or adjust the algorithmic functions performed by the implanted and/or external components, as well as the surgical approaches, in ways that would be obvious to skilled practitioners of these arts. For example, in some situations, it may be desirable to employ more than one stimulator 160, each of which could be separately controlled by means of a digital address. Multiple channels and/or multiple patterns of drug and/or electrical stimulation might thereby be programmed by the clinician and controlled by the patient in order to, for instance, deal with complex or multiple symptoms or conditions, such as may result from complex diseases, e.g., lupus, or as a result of a combination of disorders, e.g., atherosclerosis and protein S deficiency.

Various embodiments use one or more anticoagulation drugs to treat and/or prevent thromboembolic disease chronically. According to such embodiments, one or more of the infused drugs is a medication used for chronic treatment of thromboembolic disease, such as heparin, low molecular weight heparin, warfarin, aspirin, or any platelet aggregation inhibitor, such as clopidogrel and ticlopidine. Such chronic medication may be delivered at a basal rate or via periodic bolus, as programmed by a clinician. The dosage may also be programmed with other drug delivery algorithms by a clinician. Once again, sensing capabilities described earlier may be used for adjustments to chronic treatment. For example, the infusion rate of low molecular weight heparin may be modulated by a sensor that senses partial thromboplastin time (PTT) or anti-Xa assay.

Some embodiments use one or more drugs to deliver thromboembolic therapy acutely. According to such embodiments, one or more of the infused drugs is a medication used for acute treatment of thromboembolic disease, such as streptokinase or its derivatives, plasminogen activator or its derivatives, and/or urokinase or its derivatives. Such acute medication may be delivered on demand when the patient indicates such delivery is required, such as via depression of an implanted button or via a remote control that is in communication with the stimulator. The control algorithm and/or dosage may also be programmed by a clinician. If the stimulator has sensing capability, as discussed earlier, such acute medication may alternatively be delivered on demand when the stimulator senses a change in perfusion of a certain area, as programmed by a clinician. For example, tPA might be delivered by the stimulator when it senses T wave inversion and ST elevation on the ECG (abnormal ECG events, as known by those of skill in the art).

Certain embodiments use one or more drugs to deliver anticoagulation therapy acutely. According to such embodiments, one or more of the infused drugs is a medication used for acute treatment of a pathological thrombus (e.g., due to underlying thromboembolic disease), such as heparin or low molecular weight heparin or a thrombus-dissolving medication such as urokinase or tissue plasminogen activator (tPA, a.k.a., alteplase). Such acute medication may be delivered on demand when the patient indicates such delivery is required, such as via depression of an implanted button or via a remote control in communication with the stimulator. The control algorithm and/or dosage may also be programmed by a clinician. Again, if the stimulator has sensing capability, as discussed earlier, such acute medication may alternatively be delivered when the stimulator senses a change in perfusion of a certain area, as programmed by a clinician. For example, heparin might be delivered by the stimulator when it senses T wave inversion and ST elevation (i.e., abnormal events) on the ECG.

Some forms of the present systems and methods use more than one, even all, of the approaches mentioned above. As such, some combination of drug(s) to treat thromboembolic disease chronically and acutely, and to provide anticoagulation and thrombus dissolution therapy acutely may provide the best treatment to some patients. Once again, sensing capabilities described earlier may be used for adjustments to and timing of these treatments.

The drugs and other substances described above may be delivered via approaches, systems, and methods described earlier to one or more of the coronary arteries 100, one or more of the coronary veins 102, the aorta 104, the left ventricle 108, the left atrium 112, one or more of the pulmonary veins 116, the coronary sinus 120, any of the carotid arteries 122, any of the anterior, middle, or posterior cerebral arteries 124, the circle of Willis 128, any meningeal arteries (not shown), the basilar artery 134, any of the pulmonary arteries 138, the superior vena cava 140, the inferior vena cava 142, the right atrium 144, the right ventricle 146, any of the deep veins of the leg, any vessel that may influence cerebral circulation, any vessel that may influence pulmonary circulation, any vessel that may influence circulation in the lower limbs, and/or any other blood vessel or other location mentioned herein. As discussed earlier, electrical stimulation may also be applied during infusion of one or more stimulating drugs.

Furthermore, sensing means described earlier may be used to coordinate the subacute and/or chronic treatment of thromboembolic disease and related morbidities by infusion and optional electrical stimulation, and then, when appropriate, the acute treatment of thromboembolic disease symptoms, e.g., acute thrombus formation leading to sudden ischemia, as in a stroke. Alternatively, this coordination may be programmed, and not based on a sensed condition. In yet another alternative, this coordination may be controlled by the patient via the patient programmer.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient with at least one of a myocardial infarction, a stroke, and a pulmonary embolism, said method comprising:
   providing a stimulator coupled to at least one electrode and a catheter;
   configuring one or more stimulation parameters to treat at least one of a myocardial infarction, a stroke, and a pulmonary embolism;
   programming said stimulator with said one or more stimulation parameters;
   delivering with said stimulator via said catheter at least one drug to at least one tissue in accordance with said one or more stimulation parameters, said at least one drug configured to provide at least one of thrombolytic and anticoagulation treatment to said at least one tissue; and
   limiting perfusion of said at least one tissue by delivering electrical stimulation with said stimulator via said at least one electrode to said at least one tissue, wherein said electrical stimulation is configured to constrict at least one arteriole supplying said at least one tissue.

2. The method of claim 1, wherein said at least one tissue comprises at least one of a coronary artery, a coronary vein, a coronary sinus, a left ventricle, a left atrium, a surface of the myocardium, a pulmonary vein, a carotid artery, an anterior cerebral artery, a middle cerebral artery, a posterior cerebral artery, a circle of Willis, a meningeal artery, a basilar artery, a pulmonary artery, a superior vena cava, a inferior vena cava, a right ventricle, a right atrium, an aorta, a common iliac vessel, an internal iliac vessel, an external iliac vessel, a femoral vessel, a renal vessel, a celiac trunk, a middle colic artery, a superior mesenteric vessel, an inferior mesenteric vessel, a vessel that influences coronary circulation, a vessel that influences cerebral circulation, a vessel that influences pulmonary circulation, and a vessel that influences visceral circulation.

3. The method of claim 1, wherein the limiting of the perfusion of said at least one tissue is configured to increase an amount of time that said at least one drug remains in said at least one tissue.

4. The method of claim 1, wherein said delivery of said at least one drug is configured to provide acute treatment of said at least one of said myocardial infarction, said stroke, and said pulmonary embolism.

5. The method of claim 1, wherein said delivery of said at least one drug is configured to provide chronic treatment of said at least one of said myocardial infarction, said stroke, and said pulmonary embolism.

6. The method of claim 1, wherein said at least one drug comprises at least one of heparin, low molecular weight heparin, warfarin, aspirin, a platelet aggregation inhibitor, streptokinase, a streptokinase derivative, a tissue plasminogen activator (tPA), a plasminogen activator derivative, anistreplase, urokinase, and a urokinase derivative.

7. The method of claim 1, further comprising sensing at least one indicator related to at least one of said myocardial infarction, said stroke, and said pulmonary embolism, and using said at least one sensed indicator to adjust one or more of said stimulation parameters.

8. The method of claim 7, wherein said at least one sensed indicator comprises at least anticoagulation status.

9. The method of claim 7, wherein said at least on sensed indicator comprises at least one of an abnormal ECG event, an abnormal EEG event, an abnormal ultrasound echocardiogram event, an oxygen level, a flow level, a change in perfusion, a coagulation state, a left ventricular end diastolic pressure, a pulmonary capillary wedge pressure, a systemic blood pressure, a cardiac output, a Prothrombin Time (PT), an International Normalized Ratio (INR), a Partial Thromboplastin Time (PTT), an Activated Partial Thromboplastin Time (APTT), a Native Prothrombin Antigen Assay, a Specific Prothrombin Assay, an Anti-Xa Assay, a medication level, a hormone level, a D-dimer level, a lupus anticoagulant antibody level, an anti-cardiolipin antibody level, a Troponin-I level, a Troponin-T level, and a level of antibodies that bind to Troponin-I.

10. A method comprising:
    implanting a stimulator at least partially within a patient;
    providing at least one electrode and a catheter coupled to said stimulator;
    configuring one or more stimulation parameters to treat at least one of a myocardial infarction, a stroke, and a pulmonary embolism;
    programming said stimulator with said one or more stimulation parameters;
    delivering with said stimulator via said catheter at least one drug to at least one tissue in accordance with said one or more stimulation parameters, said at least one drug configured to provide at least one of thrombolytic and anticoagulation treatment to said at least one tissue; and
    limiting perfusion of said at least one tissue by delivering electrical stimulation with said stimulator via said at least one electrode to said at least one tissue, wherein said electrical stimulation is configured to constrict at least one arteriole supplying said at least one tissue;
    wherein said at least one tissue comprises at least one of a coronary artery, a coronary vein, a coronary sinus, a left ventricle, a left atrium, a surface of the myocardium, a pulmonary vein, a carotid artery, an anterior cerebral artery, a middle cerebral artery, a posterior cerebral artery, a circle of Willis, a meningeal artery, a basilar artery, a pulmonary artery, a superior vena cava, a inferior vena cava, a right ventricle, a right atrium, an aorta, a common iliac vessel, an internal iliac vessel, an external iliac vessel, a femoral vessel, a renal vessel, a celiac trunk, a middle colic artery, a superior mesenteric vessel, an inferior mesenteric vessel, a vessel that influences coronary circulation, a vessel that influences cerebral circulation, a vessel that influences pulmonary circulation, and a vessel that influences visceral circulation.

11. The method of claim 10, wherein the limiting of the perfusion of said at least one tissue is configured to increase an amount of time that said at least one drug remains in said at least one tissue.

12. The method of claim 10, wherein said delivery of said at least one drug is configured to provide acute treatment of said at least one of said myocardial infarction, said stroke, and said pulmonary embolism.

13. The method of claim 10, wherein said delivery of said at least one drug is configured to provide chronic treatment of said at least one of said myocardial infarction, said stroke, and said pulmonary embolism.

14. The method of claim 10, wherein said at least one drug comprises at least one of heparin, low molecular weight heparin, warfarin, aspirin, a platelet aggregation inhibitor, streptokinase, a streptokinase derivative, a tissue plasminogen activator (tPA), a plasminogen activator derivative, anistreplase, urokinase, and a urokinase derivative.

15. The method of claim 10, further comprising sensing at least one indicator related to at least one of said myocardial infarction, said stroke, and said pulmonary embolism, and using said at least one sensed indicator to adjust one or more of said stimulation parameters.

16. The method of claim 15, wherein said at least one sensed indicator comprises at least anticoagulation status.

17. The method of claim 15, wherein said at least on sensed indicator comprises at least one of an abnormal ECG event, an abnormal EEG event, an abnormal ultrasound echocardiogram event, an oxygen level, a flow level, a change in perfusion, a coagulation state, a left ventricular end diastolic pressure, a pulmonary capillary wedge pressure, a systemic blood pressure, a cardiac output, a Prothrombin Time (PT), an International Normalized Ratio (INR), a Partial Thromboplastin Time (PTT), an Activated Partial Thromboplastin Time (APTT), a Native Prothrombin Antigen Assay, a Specific Prothrombin Assay, an Anti-Xa Assay, a medication level, a hormone level, a D-dimer level, a lupus anticoagulant antibody level, an anti-cardiolipin antibody level, a Troponin-I level, a Troponin-T level, and a level of antibodies that bind to Troponin-I.

18. A system for treating a patient with at least one of a myocardial infarction, a stroke, and a pulmonary embolism, said system comprising:
    a stimulator configured to generate electrical stimulation and drug stimulation in accordance with one or more stimulation parameters adjusted to treat at least one of a myocardial infarction, a stroke, and a pulmonary embolism;
    a programmable memory unit in communication with said stimulator and programmed to store said one or more stimulation parameters to at least partially define said electrical and drug stimulation such that said electrical and drug stimulation are configured to treat at least one of said myocardial infarction, said stroke, and said pulmonary embolism;
    at least one electrode coupled to said stimulator; and
    a catheter coupled to said stimulator;
    wherein said stimulator is further configured to
        deliver via said catheter at least one drug to at least one tissue in accordance with said one or more stimulation parameters, said at least one drug configured to provide at least one of thrombolytic and anticoagulation treatment to said at least one tissue, and
        limit perfusion of said at least one tissue by delivering electrical stimulation via said at least one electrode to said at least one tissue, wherein said electrical stimulation is configured to constrict at least one arteriole supplying said at least one tissue.

19. The system of claim 18, wherein said at least one tissue comprises at least one of a coronary artery, a coronary vein, a coronary sinus, a left ventricle, a left atrium, a surface of the myocardium, a pulmonary vein, a carotid artery, an anterior cerebral artery, a middle cerebral artery, a posterior cerebral artery, a circle of Willis, a meningeal artery, a basilar artery, a pulmonary artery, a superior vena cava, a inferior vena cava, a right ventricle, a right atrium, an aorta, a common iliac vessel, an internal iliac vessel, an external iliac vessel, a femoral vessel, a renal vessel, a celiac trunk, a middle colic artery, a superior mesenteric vessel, an inferior mesenteric vessel, a vessel that influences coronary circulation, a vessel that influences cerebral circulation, a vessel that influences pulmonary circulation, and a vessel that influences visceral circulation.

20. The system of claim 18, wherein the stimulator is configured to limit the perfusion of said at least one tissue by increasing an amount of time that said at least one drug remains in said at least one tissue.

* * * * *